(12) United States Patent
Citterio

(10) Patent No.: US 12,667,678 B2
(45) Date of Patent: Jun. 30, 2026

(54) INHALER

(71) Applicant: Plastiape S.p.A., Osnago (IT)

(72) Inventor: Mauro Citterio, Osnago (IT)

(73) Assignee: Plastiape S.p.A., Osnago (IT)

( * ) Notice: Subject to any disclaimer, the term of this patent is extended or adjusted under 35 U.S.C. 154(b) by 648 days.

(21) Appl. No.: 18/021,343

(22) PCT Filed: Mar. 28, 2021

(86) PCT No.: PCT/EP2021/058059
§ 371 (c)(1),
(2) Date: Feb. 14, 2023

(87) PCT Pub. No.: WO2022/063438
PCT Pub. Date: Mar. 31, 2022

(65) Prior Publication Data
US 2023/0293830 A1 Sep. 21, 2023

(30) Foreign Application Priority Data
Sep. 28, 2020 (WO) ................. PCT/IB2020/059039

(51) Int. Cl.
*A61M 15/00* (2006.01)
*A61M 15/08* (2006.01)
*A61M 16/00* (2006.01)

(52) U.S. Cl.
CPC .... *A61M 15/0035* (2014.02); *A61M 15/0021* (2014.02); *A61M 15/08* (2013.01);
(Continued)

(58) Field of Classification Search
CPC .......... A61M 15/0035; A61M 15/0021; A61M 15/08; A61M 2016/0015;
(Continued)

(56) References Cited

U.S. PATENT DOCUMENTS

| | | | |
|---|---|---|---|
| 9,789,260 B1 | 10/2017 | Binier | |
| 2013/0255679 A1 | 10/2013 | Andrade et al. | |

(Continued)

FOREIGN PATENT DOCUMENTS

| | | | | |
|---|---|---|---|---|
| CN | 108475479 A | 8/2018 | | |
| WO | WO-2014184293 A1 * | 11/2014 | ............ | A61J 7/0436 |

(Continued)

OTHER PUBLICATIONS

Jun. 11, 2021—(WO) International Search Report and Written Opinion—Appl. No. PCT/EP2021/058059.

(Continued)

*Primary Examiner* — Elliot S Ruddie
(74) *Attorney, Agent, or Firm* — Banner & Witcoff, Ltd.

(57) ABSTRACT
A vibration conveyor is provided for a capsule-based, single-dose dry powder inhaler of the type comprising an inhaler body comprising a capsule chamber for receiving a dry powder formulation capsule, an inhalation channel in fluid communication with the chamber, and means for piercing a capsule in the chamber to allow outside air flow to be mixed with the contents of said capsule for inhalation thereof, means for monitoring vibrations resulting from inhalation, and means for transferring said vibrations from the inhaler body to the monitoring means. The conveyor comprises a plate interposed between the body and the means for monitoring.

17 Claims, 20 Drawing Sheets

Figure 1:
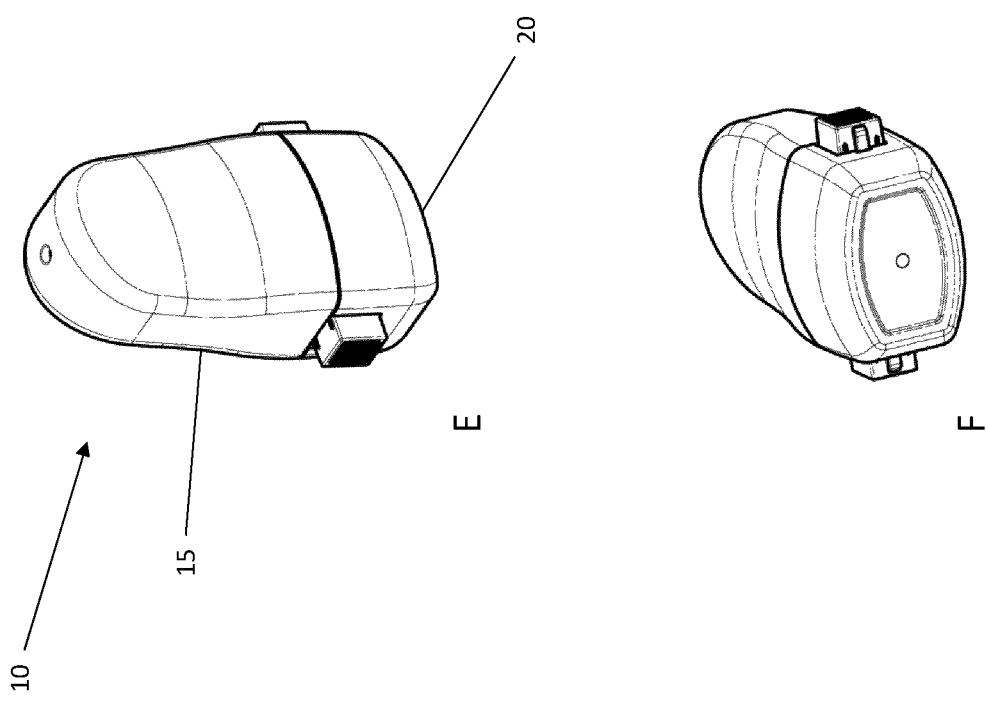
Figure 1:
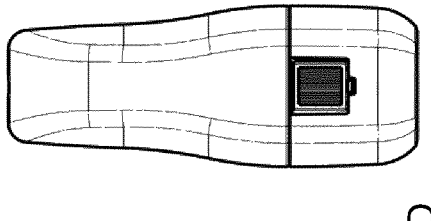
Figure 1:
Figure 1:
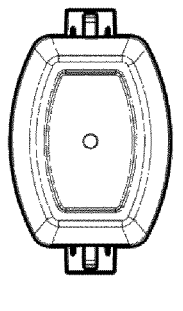
Figure 1:
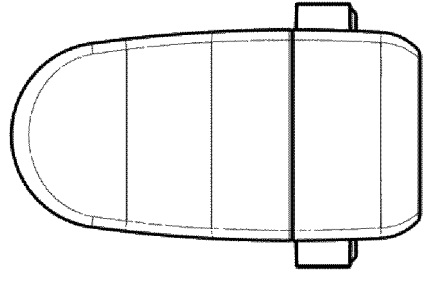
Figure 1:
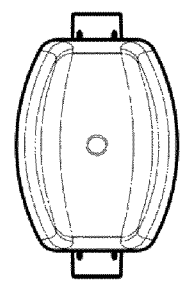

(52) U.S. Cl.
CPC ............... *A61M 2016/0015* (2013.01); *A61M 2202/064* (2013.01)

(58) Field of Classification Search
CPC .......... A61M 2202/064; A61M 11/003; A61M 2016/0018; A61M 2205/332; A61M 2205/3334; A61M 2205/3365; A61M 2205/52; A61M 2205/8206; A61M 2206/16; A61M 2230/40; A61M 15/0023; A61M 15/0025; A61M 15/0041; A61M 15/003
See application file for complete search history.

(56) References Cited

U.S. PATENT DOCUMENTS

| | | | |
|---|---|---|---|
| 2015/0136131 A1 | 5/2015 | Holakovsky et al. | |
| 2016/0129182 A1 | 5/2016 | Schuster et al. | |
| 2018/0369513 A1 | 12/2018 | Hannon et al. | |

FOREIGN PATENT DOCUMENTS

| | | | | |
|---|---|---|---|---|
| WO | WO-2016111633 A1 * | 7/2016 | ........ | A61M 15/0091 |
| WO | WO-2018160073 A1 * | 9/2018 | ........... | A61B 5/4833 |
| WO | 2022063438 A1 | 3/2022 | | |

OTHER PUBLICATIONS

Jul. 29, 2022—(WO) International Preliminary Report on Patentability—Appl. No. PCT/EP2021/058059.
Sep. 29, 2023—(CN) Office Action—App. No. 202180065228.7.
Mar. 4. 2026—Indian Examination Report Appn 202317026894.

* cited by examiner

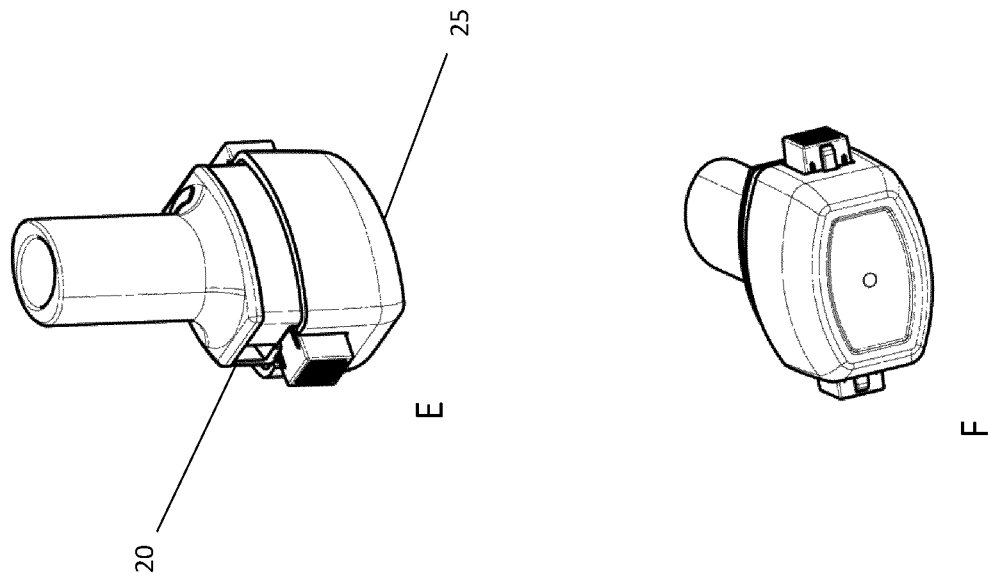
E
F
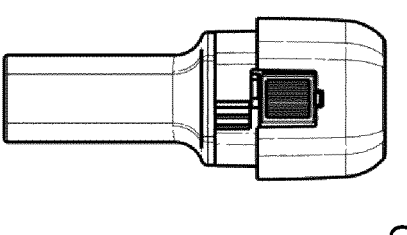
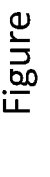
D
Figure 2
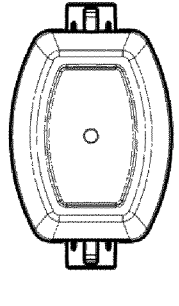
A
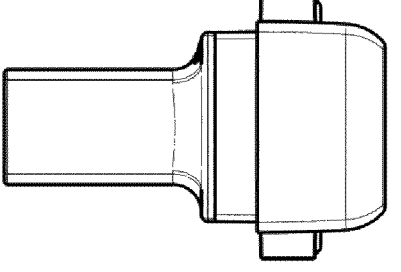
B
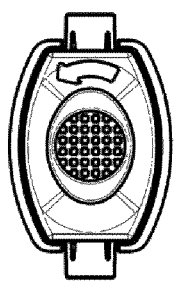
C

BODY 20

INTERPOSED ELEMENT 50

BOARD and BATTERY 55 60

BASE 25

350

360

E

F

D

A

B

C

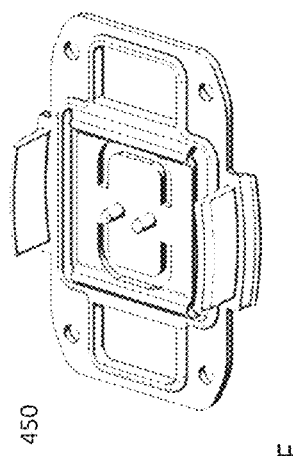
450
E
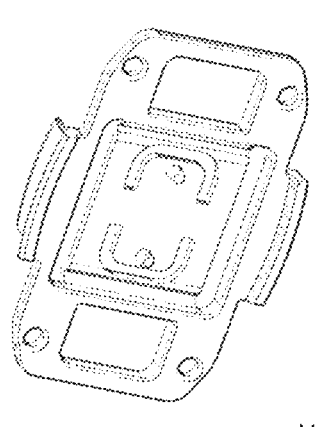
F
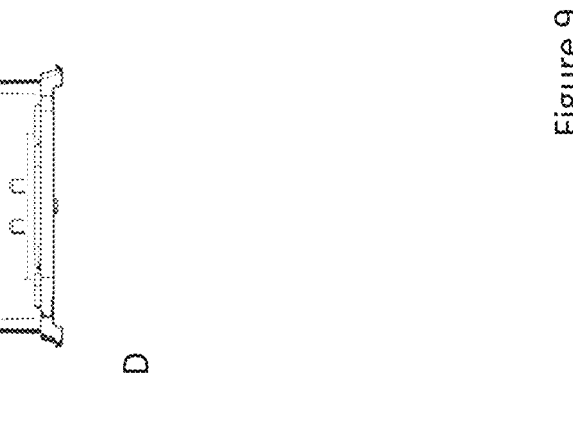
D
Figure 9
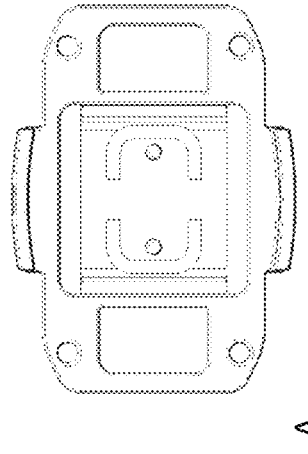
A
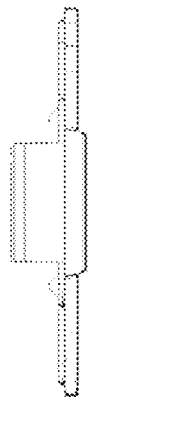
B
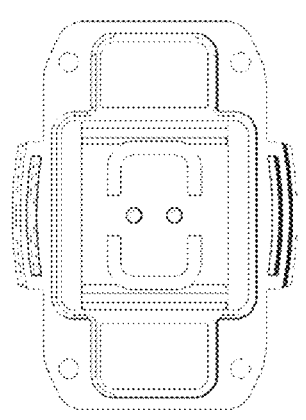
C

550

E

F

D

A

B

C

VERS. 3

870

VERS. 2

770

VERS. 1

670

910

930

920

925

INHALER

CROSS-REFERENCE TO RELATED APPLICATIONS

This application is a U.S. National Stage application under 35 U.S.C. § 371 of International Application PCT/EP2021/058059 (published as WO 2022/063438 A1), filed on Mar. 28, 2021 which claims the benefit of priority to International Application No. PCT/IB2020/059039, filed on Sep. 28, 2020. Each of these prior applications is hereby incorporated by reference in its entirety.

The present invention relates generally to a part of a dry powder inhaler and particularly, although not exclusively, to a vibration-conveying plate for a capsule-based, refillable single-dose dry powder inhaler for pulmonary or nasal delivery.

Inhaler devices for inhaling the contents of a capsule, for medical uses, are already known. For example EP 1270034 describes an inhaler configured to be loaded with a dose of medication in the form of a capsule. Such inhalers are provided with perforating means, such as needles or other sharp parts, directed towards the capsule and arranged to be actuated by the user to puncture the capsule. During subsequent inhalation, turbulent airflow causes the capsule to spin and release the powder for inhalation by the user. This allows for the gradual release and delivery of a precise dose of medication to a patient with a wide range of capsule materials and powder formulation.

An aspect of the present invention provides a vibration conveyor for a capsule-based, single-dose dry powder inhaler of the type comprising an inhaler body comprising a capsule chamber for receiving a dry powder formulation capsule, an inhalation channel in fluid communication with the chamber, and means for piercing a capsule in the chamber to allow outside air flow to be mixed with the contents of said capsule for inhalation thereof, means for monitoring vibrations resulting from inhalation, and means for transferring said vibrations from the inhaler body to the monitoring means, in which the conveyor comprises a plate interposed between the body and the means for monitoring.

The present invention does not relate to the general idea of an inhaler providing inhalation data, nor to the specific use of monitoring means (such as accelerometers) to detect and transform inhaler vibrations into inhalation performance data, but rather to particular ways of transferring these vibrations within the inhaler to said monitoring means.

The interposed plate may comprise one or more contact pins for contacting the capsule chamber.

The interposed plate may comprise one or more cantilever beams.

The or each beam may be corrugated.

A further aspect provides a capsule-based, single dose dry powder inhaler provided with a conveyor as described and defined herein.

The inhaler may further comprise a base.

The inhaler body may be receivable by the base.

The interposed plate may be attached or attachable to the body.

The inhaler may further comprise a mouthpiece or nosepiece.

The nosepiece/mouthpiece may be movable to provide at least two operating condition, an open condition in which the capsule chamber can be accessed to engage therein a new capsule or to withdraw therefrom a used capsule, and a closed use condition.

In some embodiments the nosepiece/mouthpiece can rotate with respect to said inhaler body.

The means for piercing comprise perforating needles may be designed for transversely sliding against the biassing of resilient elements.

The means for piercing may comprise perforating needles designed for transversely sliding against the biassing of resilient elements (e.g. springs or the like). A corresponding push-button may be provided for each perforating needle.

Each perforating needle may have a contour similar to that of a hypodermic needle, including a bevelled tip, for facilitating a perforation of a coating of a capsule.

Some embodiments comprise an add-on module which can be clipped onto an inhaler and contain electronic parts.

The means for monitoring vibrations may comprise a printed circuit board.

Transfer of vibrations occurs from the capsule chamber (for example) to a printed circuit board, and to an accelerometer installed on it.

Rigid or elastic connections between the plate and a printed circuit board may be provided. Rigid and elastic connections may be achieved, for instance, through material properties (e.g. insert made of ceramics vs. insert made of rubber) or through a convenient design.

Elasticity is the ability of a body to resist a distorting influence and to return to its original size and shape when that influence or force is removed. This is in contrast to plasticity, in which the object fails to do so and instead remains in its deformed state.

A solid material might undergo an elastic or a plastic deformation depending on the tensile stress applied to it. Also extremely rigid materials are elastic, at least in some regions of the stress/strain curve.

Different Levels of Rigidity May be Achieved Through Material Properties.

Rigidity of solid materials in a linear region can be modeled by the Hooke's Law. Hooke's Law states that stress is proportional to strain. Young's Modulus [E], or Modulus of Elasticity, measures the tensile stiffness of a solid material and quantifies the relationship between stress ($\sigma$) and axial strain ($\varepsilon$) in the linear elastic region of a material: $\sigma = E\varepsilon$.

Force applied to the relevant portions of the interposed elements will be modeled by the following simplified model:

$$\sigma = E\varepsilon$$

$$\varepsilon = DL / L_0$$

$$\sigma = F / A$$

$$=> F = \sigma A = E\varepsilon A = E * DL / Lo * A = E * DL * A / Lo$$

One option in order to achieve different levels of rigidity or flexibility according to the vibration needs of the specific inhaler versions may be to use an interposed element manufactured using materials having a different Young's Modulus.

An example rigid component may have an infinite Young's Modulus. Infinite is a theoretical concept not available in nature. Good approximations of this status can be represented by a material like diamond (Young's Modulus of diamond is in the range of 1050-1210 GPa).

Young's Module varies from material to material. If, for example, we exclude expensive materials like diamond and we assume few discrete levels are sufficient to cover all the potential requirements, different materials might be selected to manufacture the component which is connecting the capsule chamber to the printed circuit board (interposed element): a rubber (Young's Modulus of conventional rubbers in the range of 0.01-0.1 GPa); polyolefins like Low Density Polyethylene (LDPE) and High Density Polyethilene (HDPE) (YM ranges from 0.1 to 1.3 GPa); a rigid thecnopolymer like Acrylonitrile Butadiene Styrene or Polycarbonate (Young's Modulus in the range of 2.4 GPa) or Polyoxymethylene (YM in the range of 2.7-2.9 GPa); up to Aluminium (YM in the range of 69 GPa); Copper (YM in the range of 120 GPa) and Stainless steel such as AISI 302 or AISI 304 or AISI 316 (YM in the range of 200 GPa).

The large scale manufacturing of components made of different materials may require different technologies. In the above cases, metal components may be conveniently manufactured using an automated CNC milling machine, rubber component might be conveniently manufactured by extrusion and cutting of a rubber layer and Polypropylene or Polyoxymethylene or Acrylonitrile Butadiene Styrene plastic components might be conveniently manufactured by injection moulding. Furthermore, also the components manufactured by injection moulding would hardly be manufactured using the same equipment or mould since shrinkage rate of different plastic resins are different, ideal injection gates have different dimensions, and ideal mould conditioning temperatures significantly different (e.g. mould cooled 15° C. to 40° C. for PP and conditioned at 80-120° C. for Polyoxymethylene).

Different Levels of Rigidity Achieved Through Convenient Design.

Instead of or in addition to using different raw materials, different levels of rigidity or flexibility of the interposed element may be achieved through a convenient design.

Some designs provide an interposed element which can offer a different degree of rigidity depending on the different set-up of the same equipment and all variants can be manufactured using the same technology.

In some embodiments the proposed interposed element between capsule chamber and printed circuit board might be either metallic or made of a polymer resin but polymer resins are lighter and cheaper and therefore represent the preferred option.

A design containing cantilever beams might be used to regulate flexibility of the preloading, for example.

The so-called Beams Equation can be used to predict the deflection of the Beam while the Young's modulus of the selected material can be used to predict the stress/strain ratio.

In case of complicated beam shapes, FEM analysis can be implemented.

If we consider a simple cantilever beam the following equations can be applied:

$$\sigma = E\varepsilon$$

$$Y = FL^3 / 3EI$$

$$I = bh^3 / 12$$

$$=> F = \sigma A = E\varepsilon A = E * b * Y * I / 4 * h^3 / L^3$$

Where:
I=Moment of Inertia
Y=Beam deflection
L=Length of the beam
b=width of the beam h=thickness of the beam Therefore, once a material has been selected, flexibility can be easily increased or decreased working either on the cross section of the beam or on its extension.

In some embodiments an interposed element could be conveniently moulded using a dedicated tool on conventional injection moulding machines. Some designs do not require mould screwing mechanisms or sliders which would make the mould more complicated and expensive.

Interposed element/s could, for example, be manufactured using a commodity material such as Polyethylene or Polypropylene or a stronger material such as Acrylonytryle Butadiene Styrene or a technopolymer such as Polyoxymethylene or Polyamide or Polybutylene terephthalate.

Cantilever extension/s, where present, can be easily and conveniently adjusted on an injection moulding tool thanks to interchangeable and cheap mould inserts that can be replaced in the tool cavity.

In this way simple and interchangeable tool inserts can be used to manufacture a set of different interposed elements, all manufactured with the same raw material and the same mould, but having significantly different hardness.

Additional design options, where both of two contacting pins are positioned on the same element but upper pins and lower pins are connected by a single beam having two opposite supports.

Corrugated beams might be preferred in order to enhance flexibility of the structure.

Example of advantages/differences of design vs. material hardness:
1. Versions manufactured with the same technology
2. Versions manufactured using the same mould
3. Possibility to use cavity inserts to create an easy and cheap change of format
4. Possibility to manufacture infinite rigidity values, on a continuous scale, by adjusting beams length on the inserts
5. Possibility to work both on linear variables (e.g. E, b) or cubic variables (e.g. h, L) that can offer an higher degree of variability.

Different aspects and embodiments of the invention may be used separately or together.

Further particular and preferred aspects of the present invention are set out in the accompanying independent and dependent claims. Features of the dependent claims may be combined with the features of the independent claims as appropriate, and in combinations other than those explicitly set out in the claims.

The present invention is more particularly shown and described, by way of example, in the accompanying drawings.

The example embodiments are described in sufficient detail to enable those of ordinary skill in the art to embody and implement the systems and processes herein described. It is important to understand that embodiments can be provided in many alternative forms and should not be construed as limited to the examples set forth herein.

Accordingly, while embodiments can be modified in various ways and take on various alternative forms, specific embodiments thereof are shown in the drawings and described in detail below as examples. There is no intent to limit to the particular forms disclosed. On the contrary, all modifications, equivalents, and alternatives falling within the scope of the appended claims should be included. Elements of the example embodiments are consistently denoted by the same reference numerals throughout the drawings and detailed description where appropriate.

Unless otherwise defined, all terms (including technical and scientific terms) used herein are to be interpreted as is customary in the art. It will be further understood that terms in common usage should also be interpreted as is customary in the relevant art and not in an idealised or overly formal sense unless expressly so defined herein.

In the description, all orientational terms, such as upper, lower, radially and axially, are used in relation to the drawings and should not be interpreted as limiting on the invention.

Figure 3:
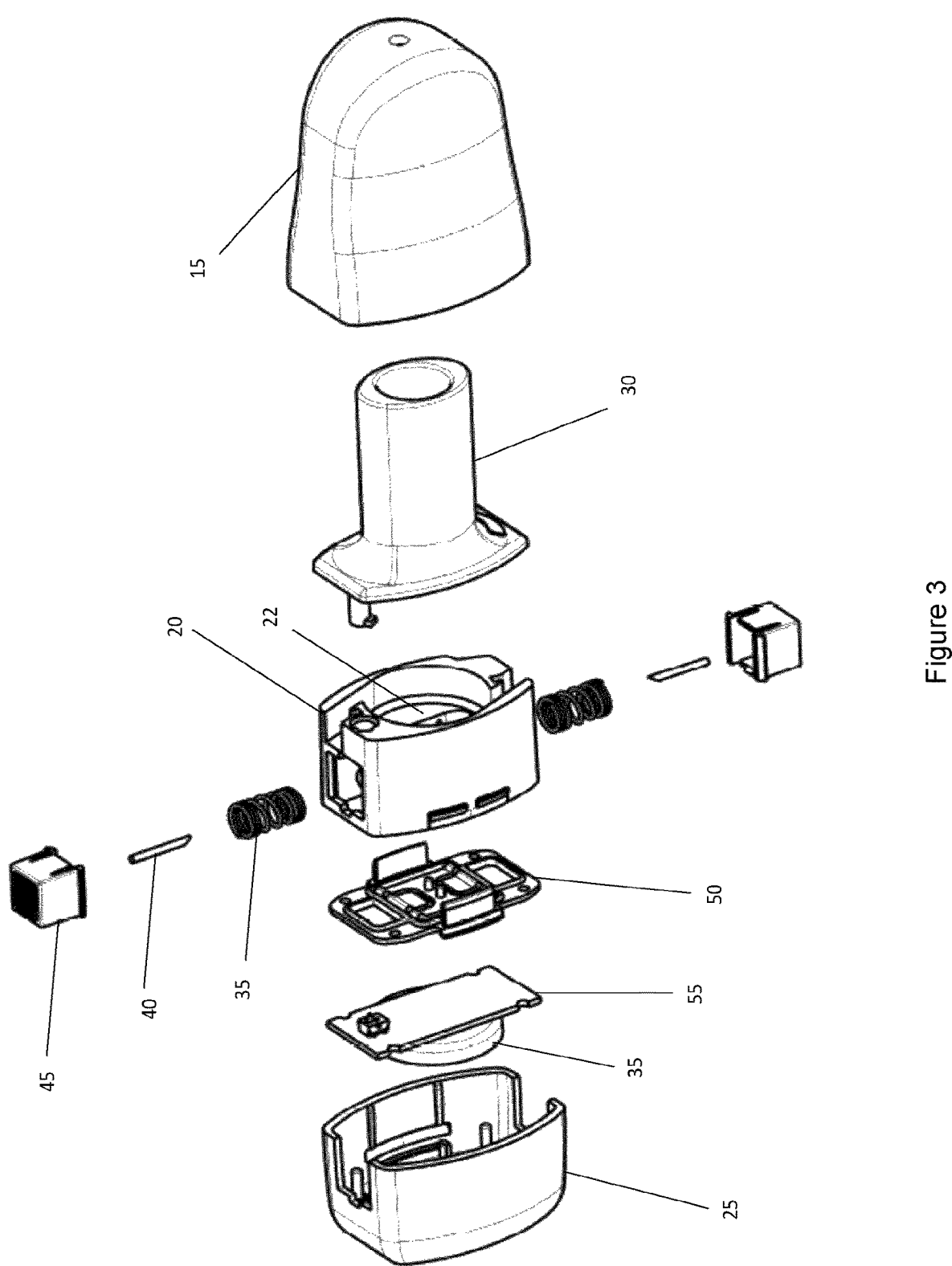

FIGS. 1 to 3 show an inhaler generally indicated 10 and comprising: a cover 15; a body 20; a base 25; a mouthpiece 30; springs 35; piercing needles 40; press buttons 45; vibration-conveying plate 50; printed circuit board 55; battery 60.

The general concept works thanks to an accelerometer 57 provided on the board 55 and arranged to measure mechanical oscillation determined at least by the agitated motion of a capsule within a capsule chamber 22 formed in the body 20 of the inhaler and/or also by a flow of air through the inhaler chamber during inhalation.

Transfer of vibrations occurs from the capsule chamber 22 to the printed circuit board 55, and therefore to the accelerometer 57 installed on it.

Different air flow resistances, different sizes of the capsules or different drugs might induce or require different inhalation flow rates (for instance from 20 l/min to 120 l/min). Rotation speed of the capsule is directly proportional to the airflow rate.

Different airflow rates and different rotation speeds of the capsule are expected to generate different level of vibrations and therefore might require differences in the preloading between the capsule chamber and the printed circuit board.

Figure 4:
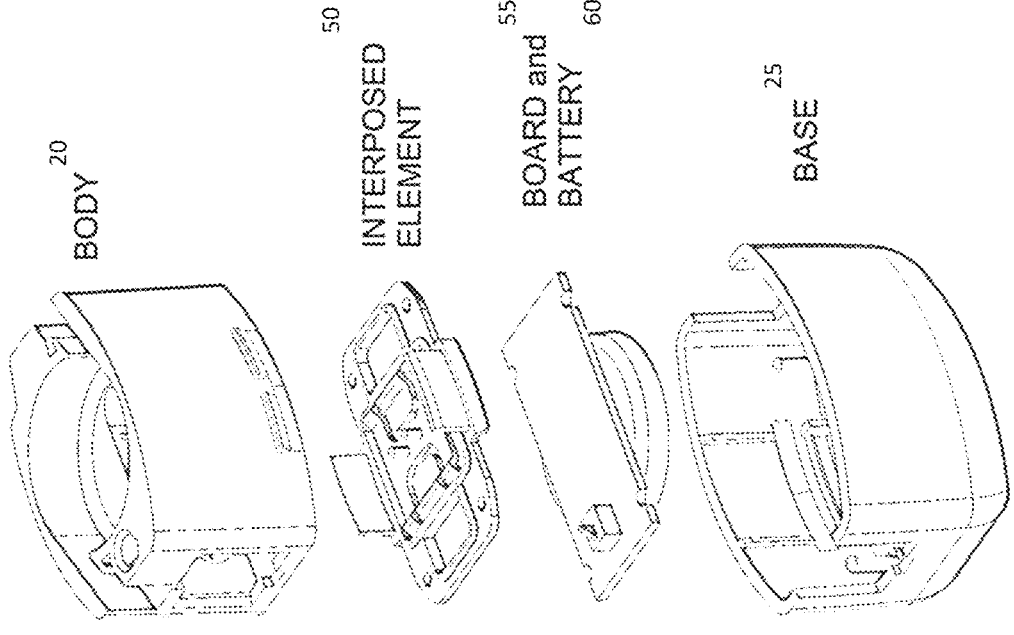
Figure 5:
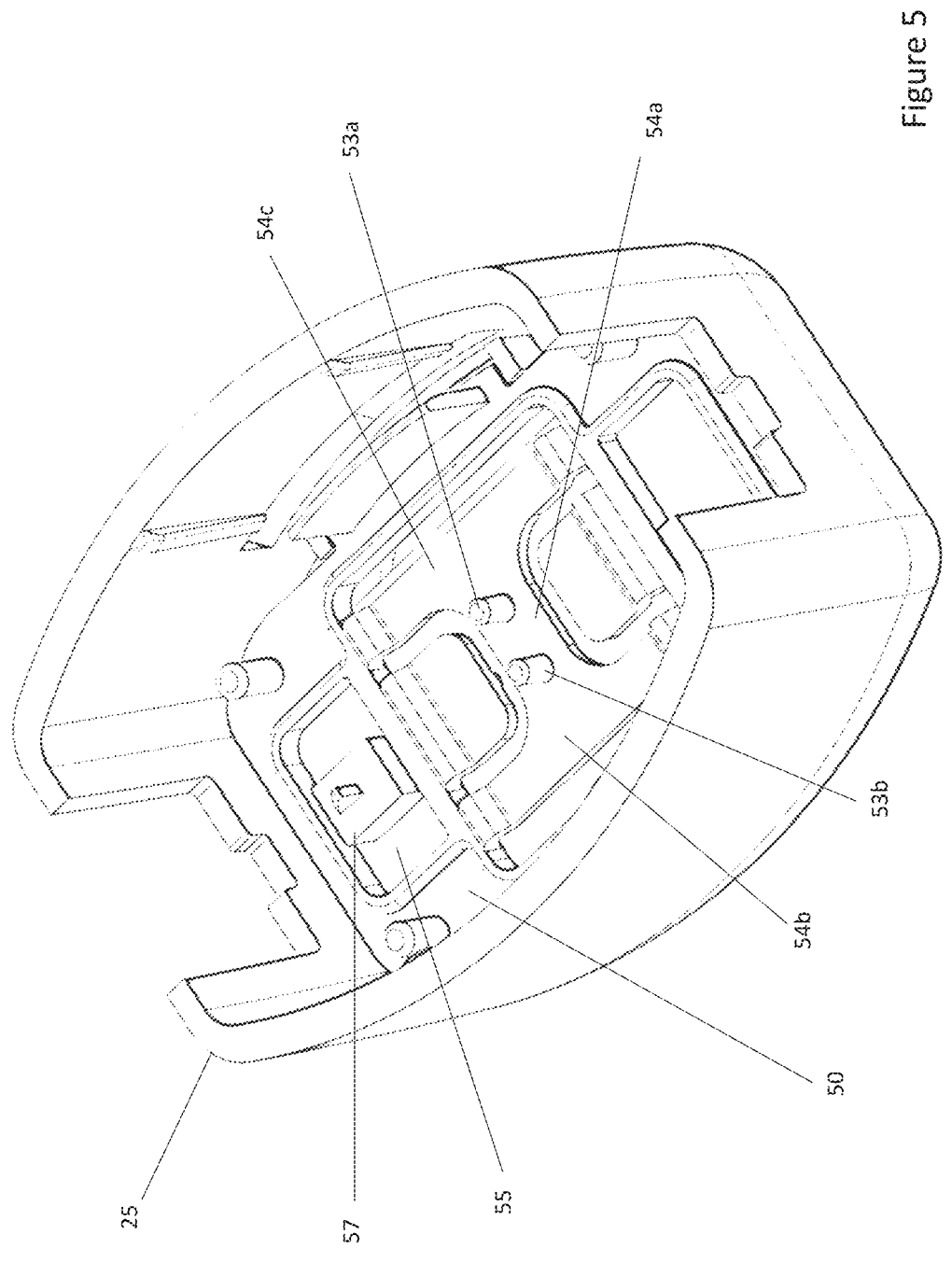
Figure 6:
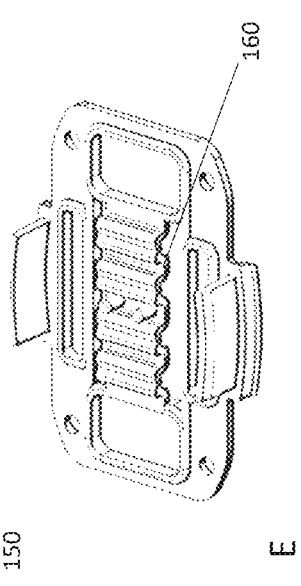
Figure 6:
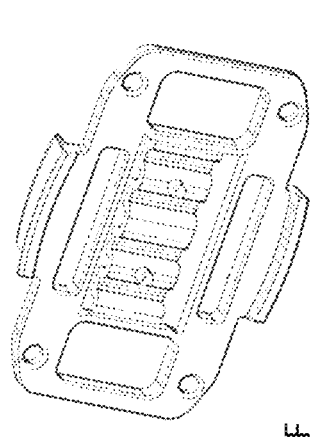
Figure 6:
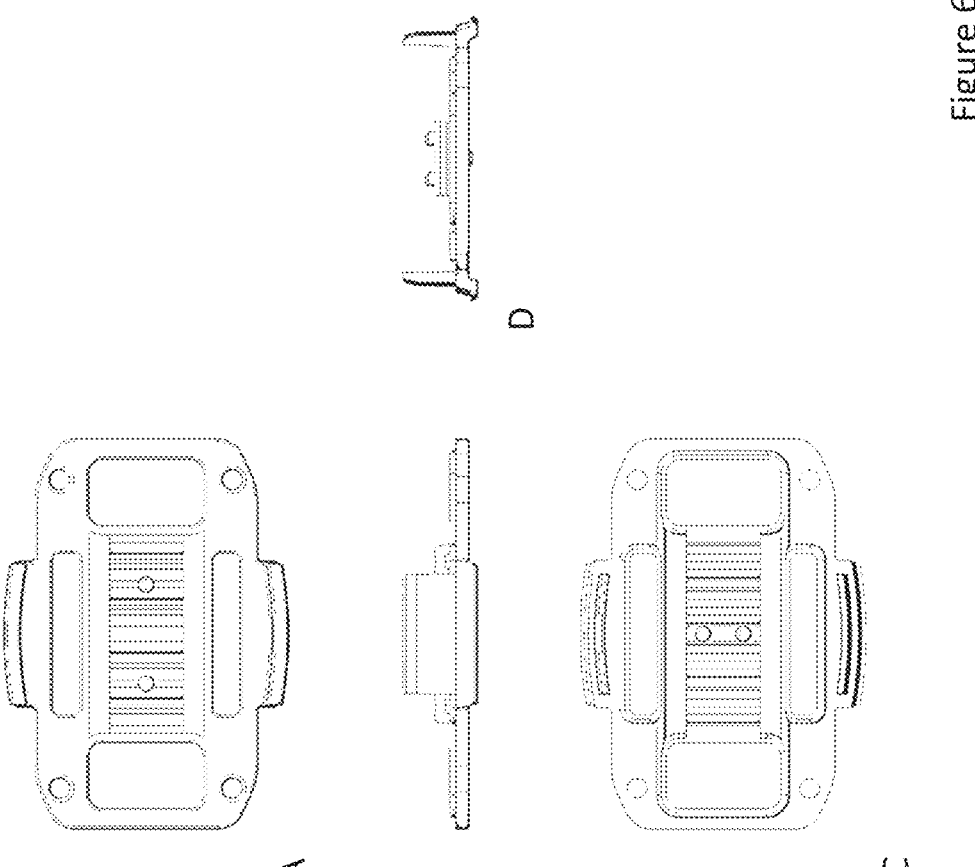
Figure 7:
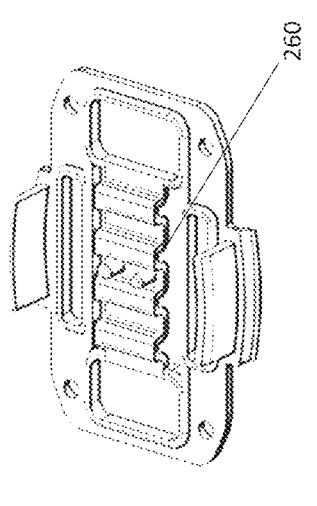
Figure 7:
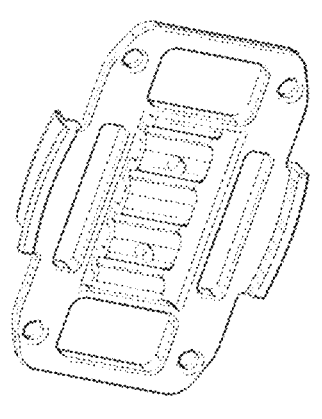
Figure 7:
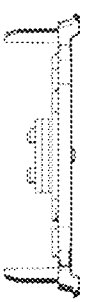
Figure 7:
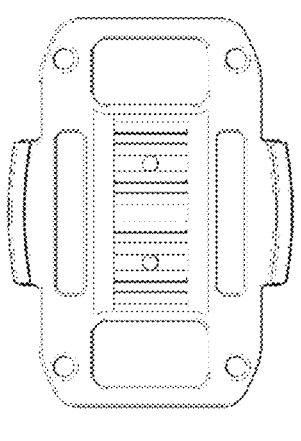
Figure 7:
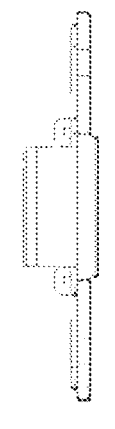
Figure 7:
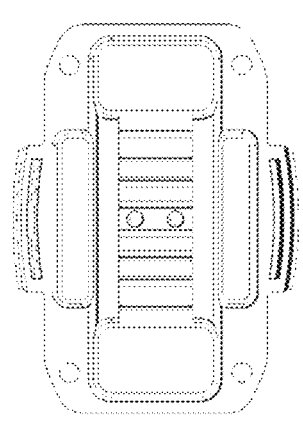

Referring also to FIGS. 4 and 5 the base 25 is generally cup-like with two opposed notches 26 (which receive the capsule piercing mechanism). From the interior of a bottom face four pins 27 are upstanding. The plate 50 is generally rectangular and has four holes 51 corresponding to the pins 27. The plate 50 has opposed wings 52 for clipping it into the base on top of the board 55.

In this embodiment the plate 50 is generally symmetrical about a midline. The plate 50 includes two (in this embodiment) upstanding vibration receiving pins 53.

Both of two contacting pins 53 are positioned on the same element but upper pin 53a and lower pin 53b are connected by a single beam 54a having two opposite supports 54b, 54c, forming a generally H-shape element.

The base clips onto the body.

Capsule installation, capsule puncturing and inhalation is generally as described in relation to EP1270034.

Different interposed plates are shown in FIGS. 6 to 10.

Figure 8:
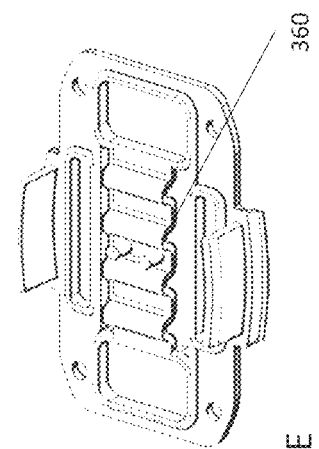
Figure 8:
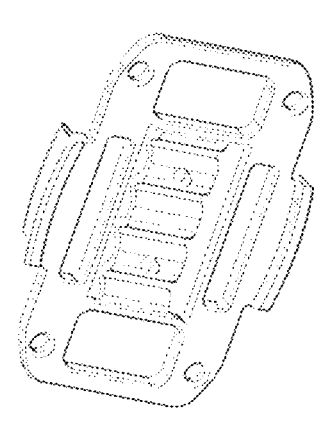
Figure 8:
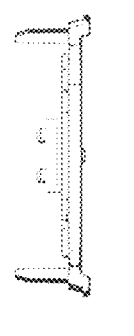
Figure 8:
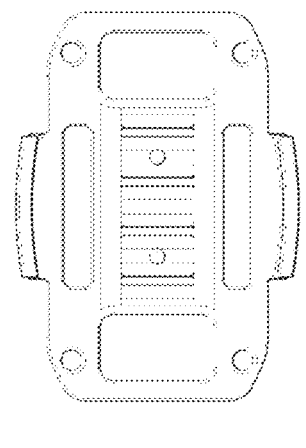
Figure 8:
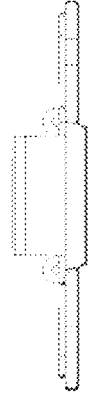
Figure 8:
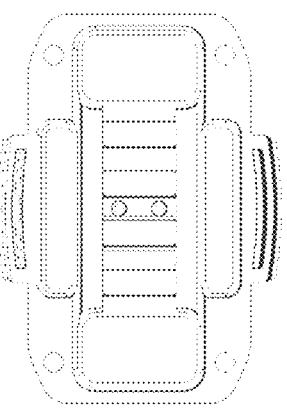
Figure 10:
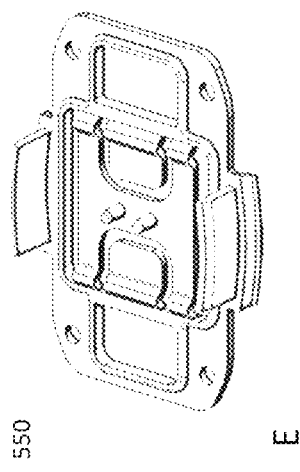
Figure 10:
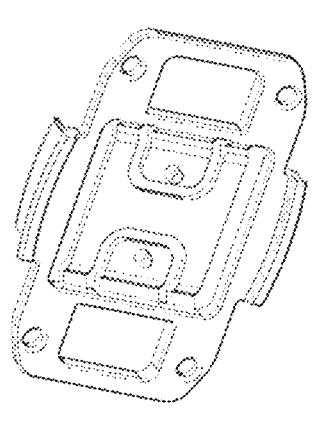
Figure 10:
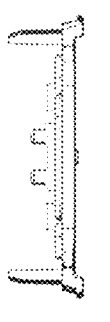
Figure 10:
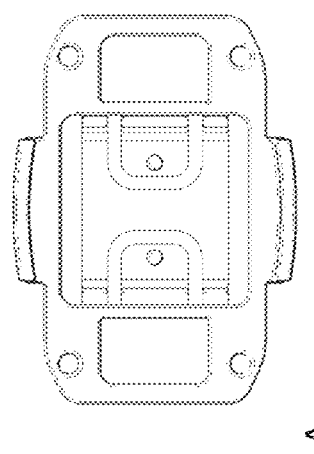
Figure 10:
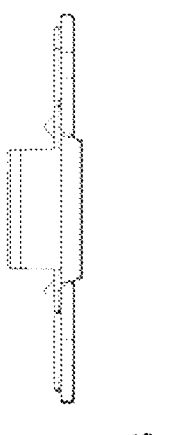
Figure 10:
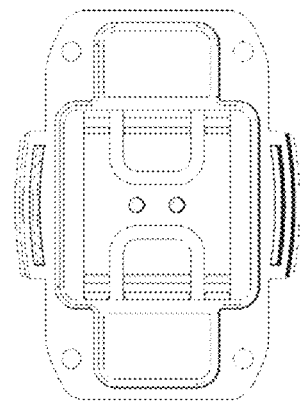

Corrugated beams might be preferred in order to enhance flexibility of the structure—embodiments shown in FIGS. 8-10. Cantilever beams 160, 260, 360, from which contact pins are upstanding, are used to regulate flexibility of the preloading.

Figure 11:
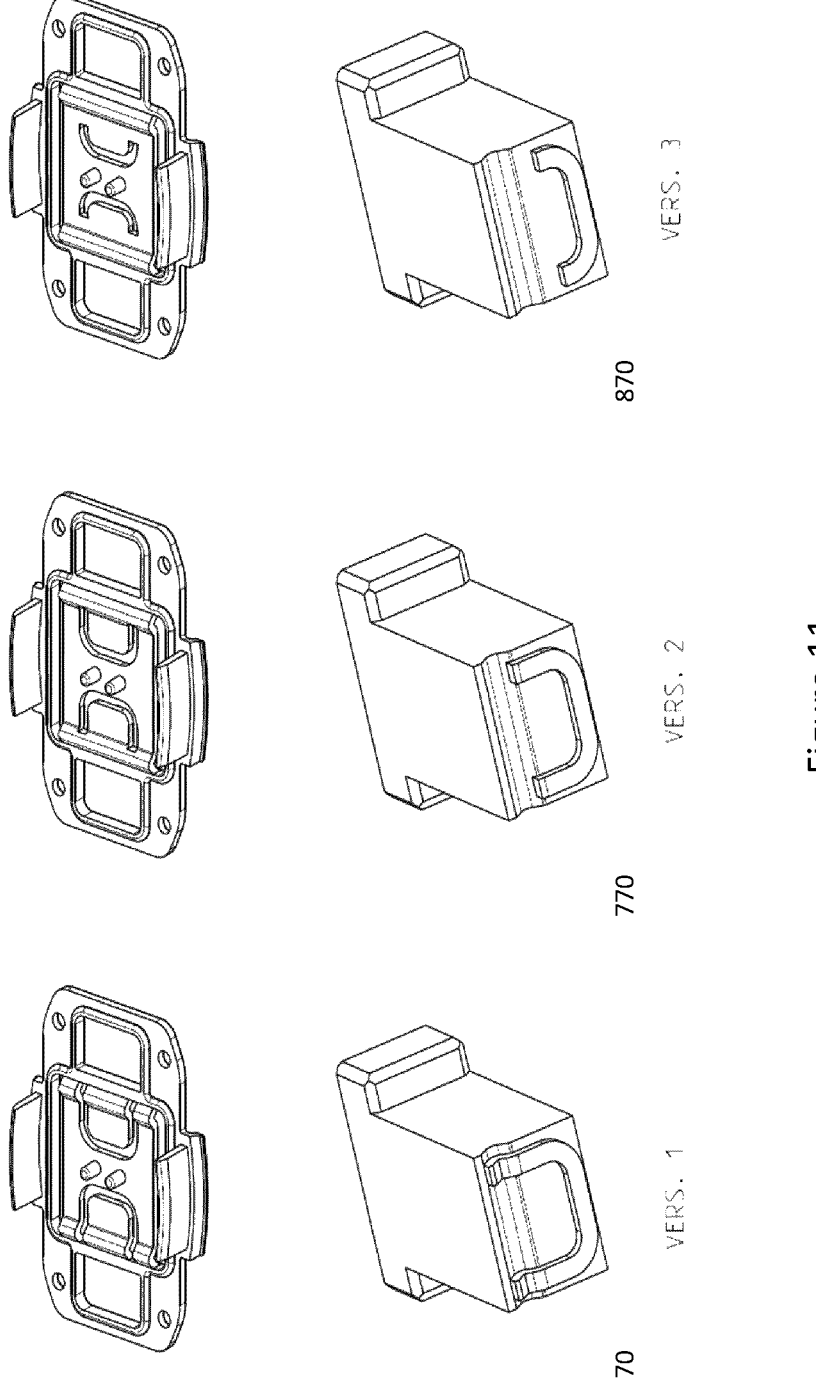
Figure 12:
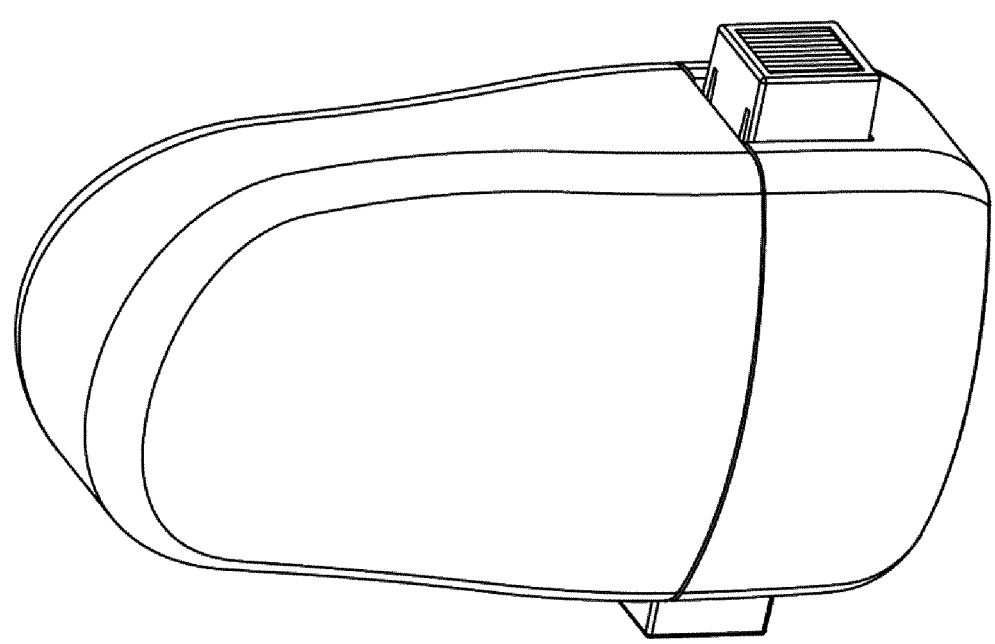
Figure 13:
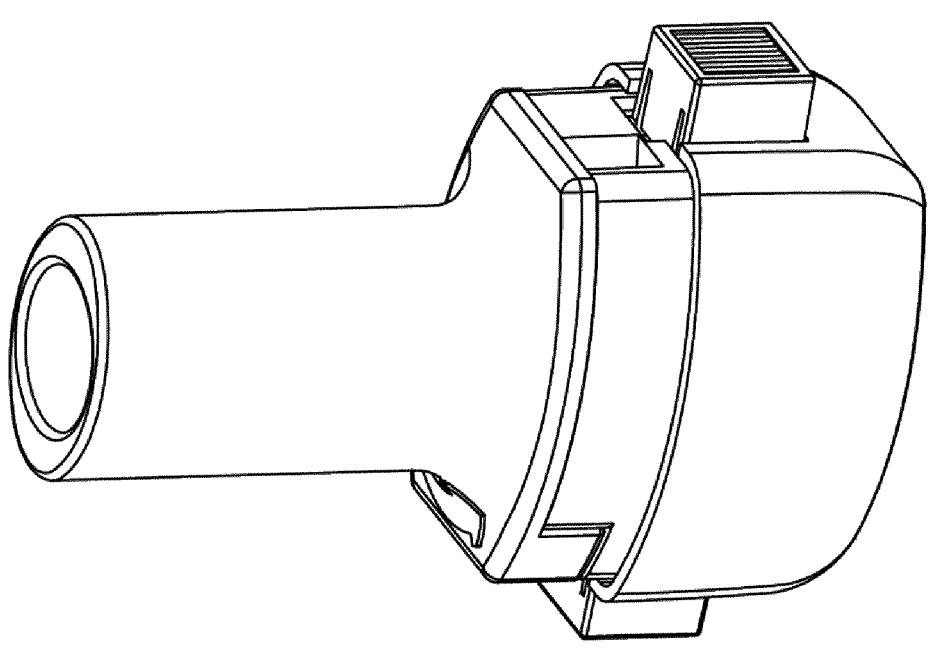
Figure 14:
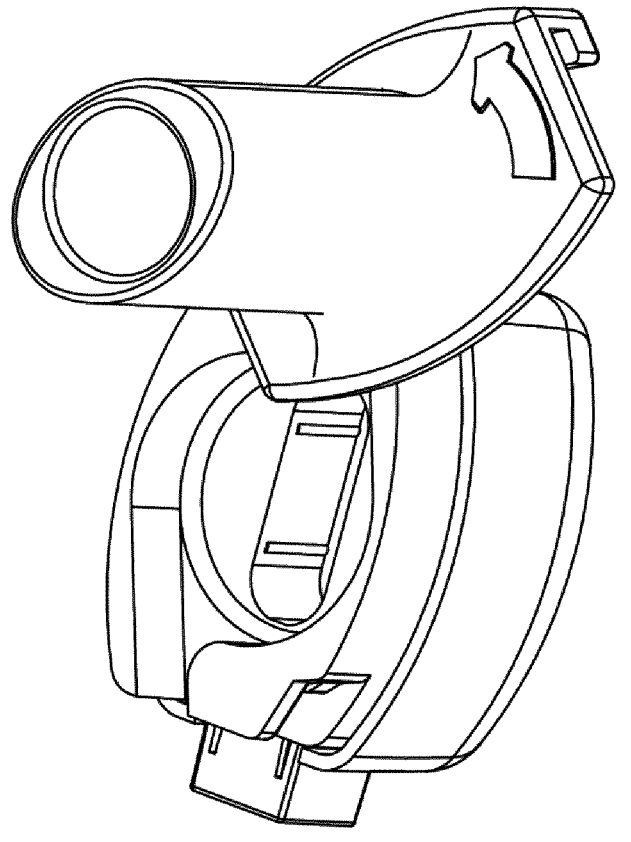
Figure 15:
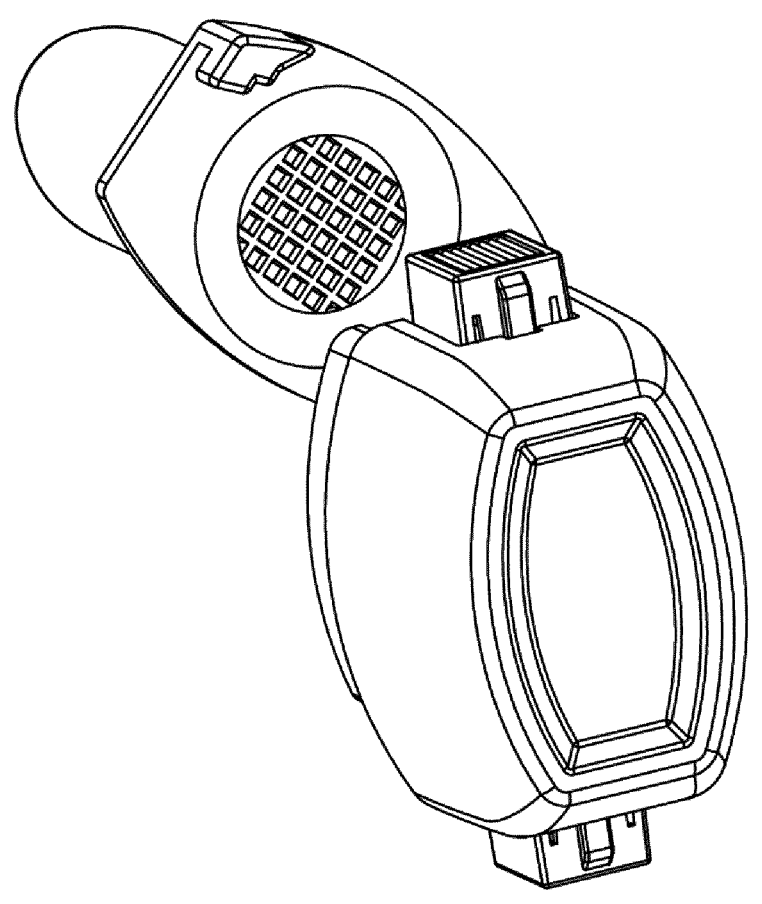
Figure 16:
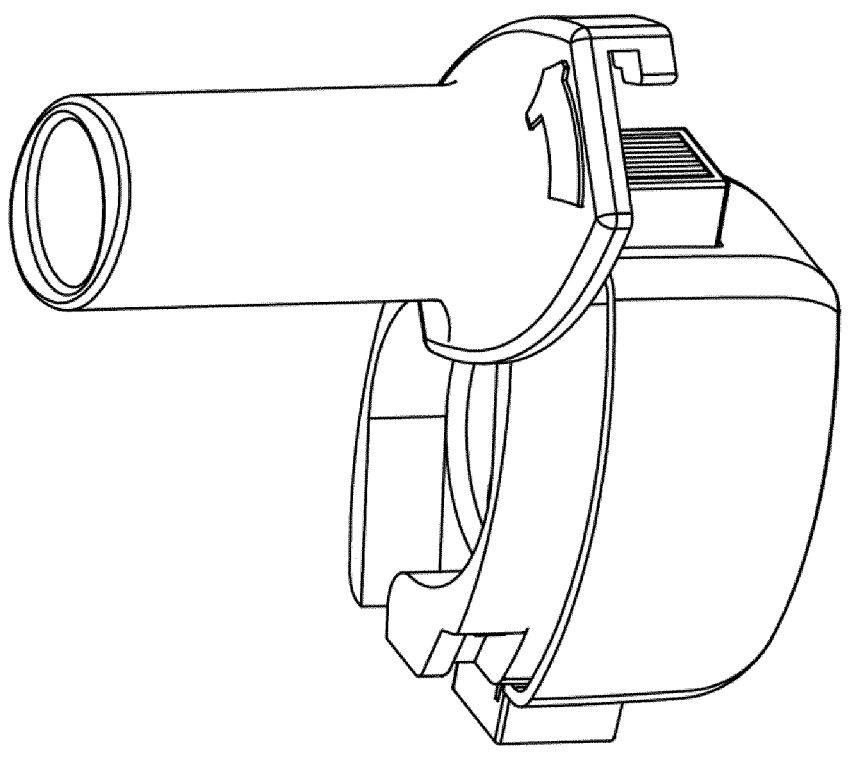
Figure 17:
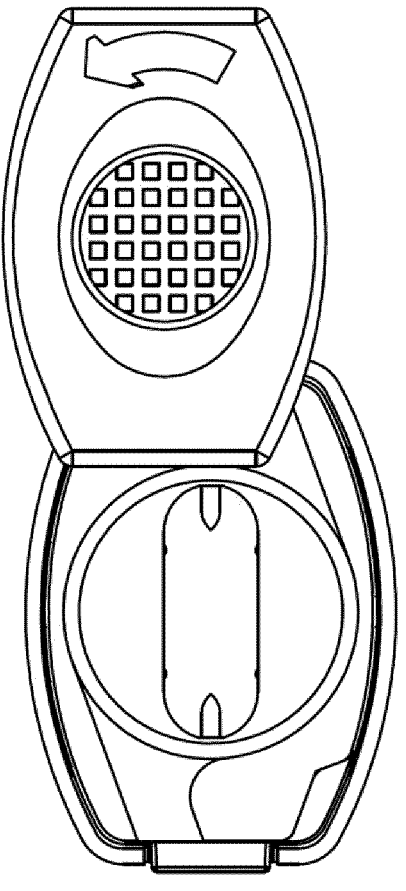
Figure 18:
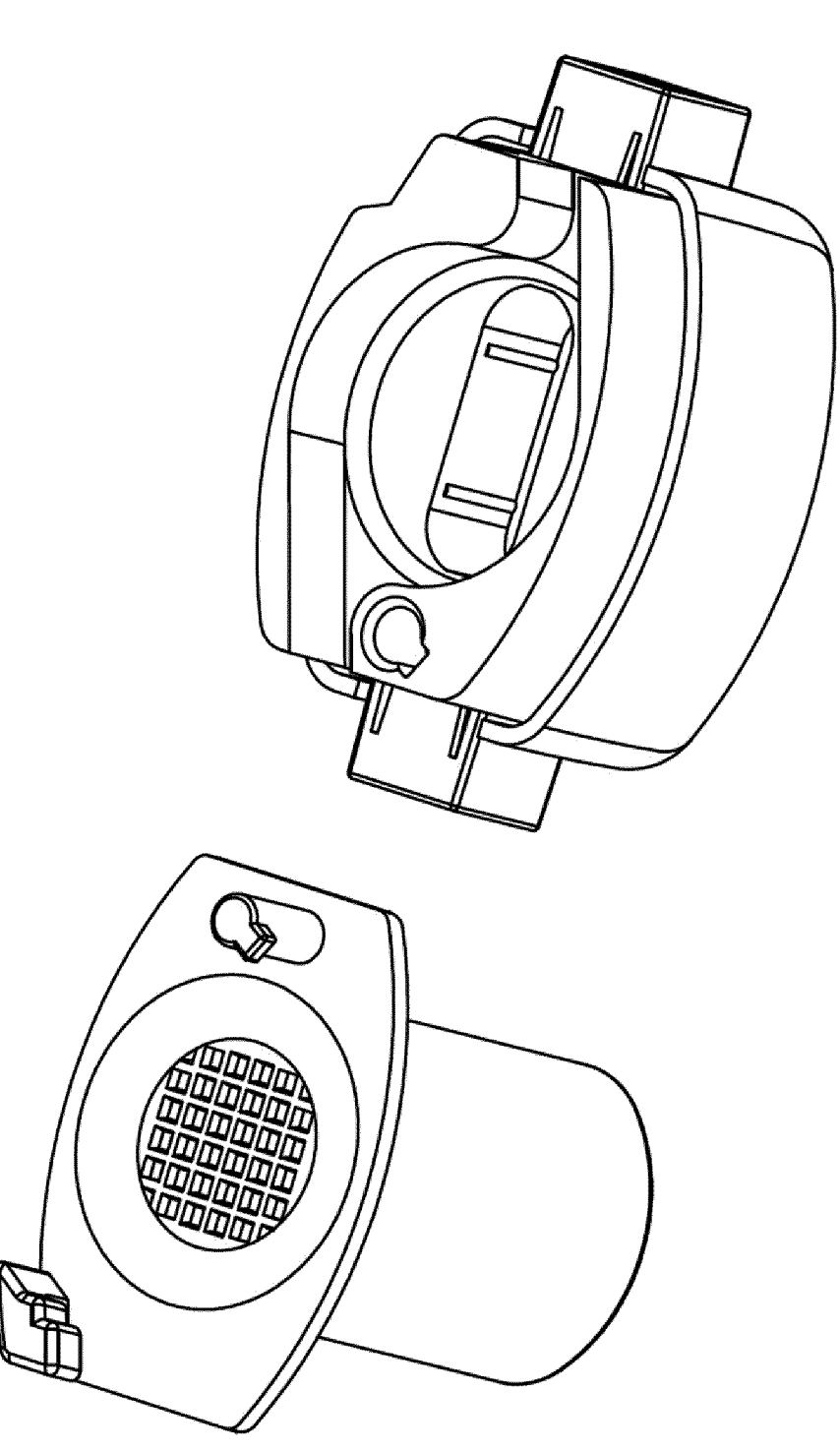
Figure 19:
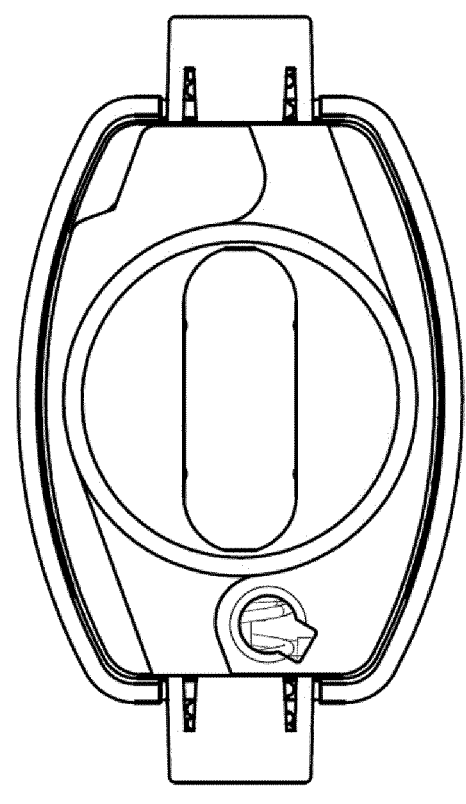
Figure 19:
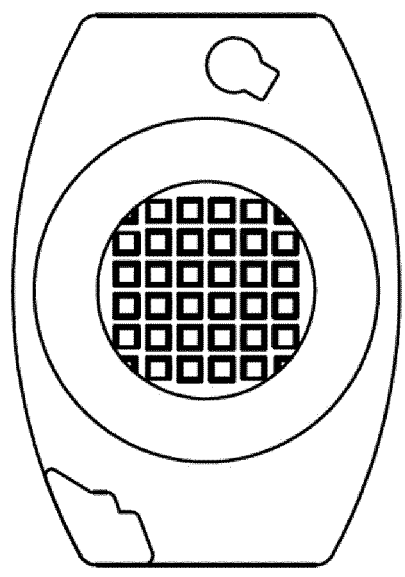
Figure 20:
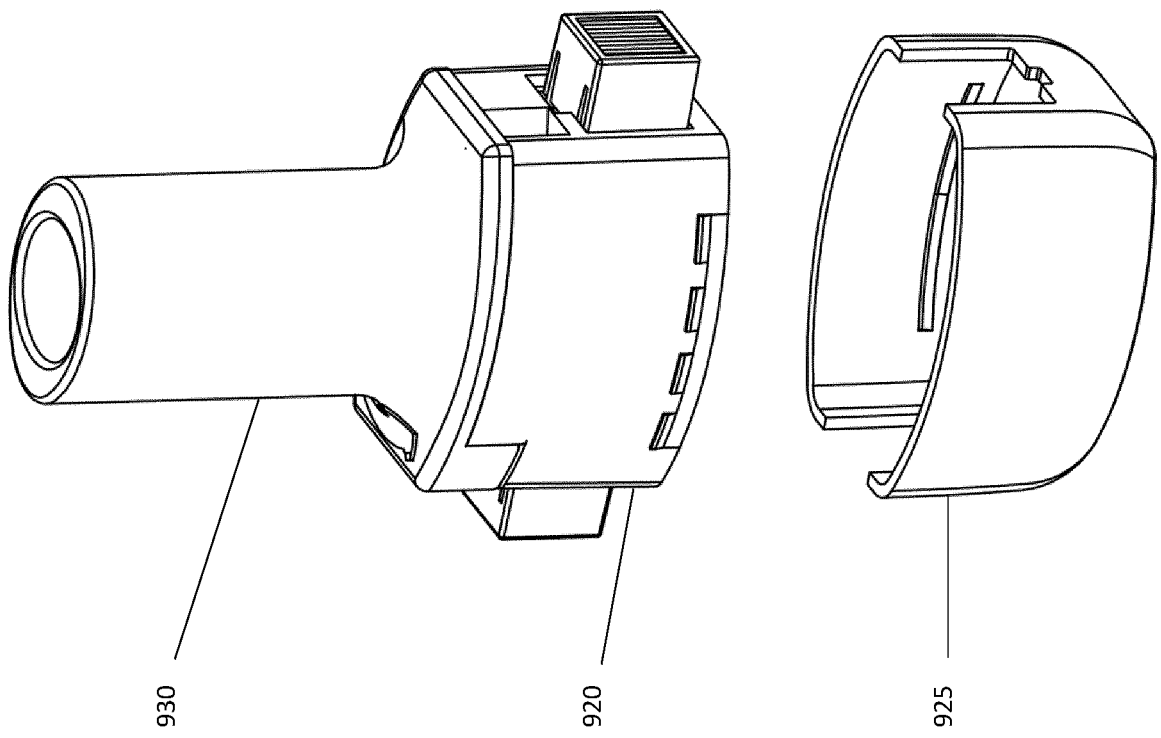

In FIG. 11 interchangeable mould inserts 670, 770, 870 are shown and can be used to create interposed elements having different rigidities.

FIGS. 12 to 20 show an inhaler 910 formed according to a further embodiment and operating in a similar way to the inhaler 10 of FIGS. 1 to 3.

Although illustrative embodiments of the invention have been disclosed in detail herein, with reference to the accompanying drawings, it is understood that the invention is not limited to the precise embodiments shown and that various changes and modifications can be effected therein by one skilled in the art without departing from the scope of the invention as defined by the appended claims and their equivalents.

The invention claimed is:

1. A capsule-based, single-dose dry powder inhaler (10) comprising an inhaler body (20) comprising a capsule chamber (22) for receiving a dry powder formulation capsule, an inhalation channel in fluid communication with the chamber, and means (40) for piercing a capsule in the chamber to allow outside air flow to be mixed with the contents of said capsule for inhalation thereof, means (57) for monitoring vibrations resulting from inhalation, and means for transferring said vibrations from the inhaler body to the monitoring means, in which the means for transferring said vibrations is a vibration conveyor (50), in that the conveyor comprises a plate interposed between the body and the means for monitoring, and in that the interposed plate comprises one or more cantilever beams (160, 260, 360).

2. An inhaler as claimed in claim 1, further comprising a base (25).

3. An inhaler as claimed in claim 2, in which the inhaler body (20) is receivable by the base (25).

4. An inhaler as claimed in claim 2, in which the interposed plate (50) is attachable to the base (25).

5. An inhaler as claimed in claim 1, in which the interposed plate (50) is attachable to the body (20).

6. An inhaler as claimed in claim 1, further comprising a mouthpiece (30) or nosepiece.

7. An inhaler as claimed in claim 6, in which said nosepiece or mouthpiece (30) is movable to provide at least two operating conditions: an open condition in which the capsule chamber (22) can be accessed to engage therein a new capsule or to withdraw therefrom a used capsule; and a closed, use condition.

8. An inhaler as claimed in claim 7, in which said nosepiece or mouthpiece (30) can rotate with respect to said inhaler body (20).

9. An inhaler as claimed in claim 1, in which the means for piercing comprise perforating needles (40) designed for transversely sliding against the biassing of resilient elements (35).

10. An inhaler as claimed in claim 1, in which the interposed plate comprises one or more contact pins (53) for contacting the capsule chamber (22).

11. An inhaler as claimed in claim 1, in which the or each cantilever beam has an extension.

12. An inhaler as claimed in claim 1, in which the or each cantilever beam is corrugated.

13. A vibration conveyor (50) for transferring inhalation vibrations from the inhaler body to the vibration monitoring means of a capsule-based, single-dose dry powder inhaler according to claim 1, in which the conveyor comprises a plate which can be interposed between the body and the means for monitoring, and in which the interposed plate comprises one or more cantilever beams (160, 260, 360).

14. A vibration conveyor (50) for transferring vibrations from an inhaler body to a monitoring means of a capsule-based, single-dose dry powder inhaler, in which the conveyor comprises a plate which can be interposed between the body and the means for monitoring, and in which the interposed plate comprises one or more cantilever beams (160, 260, 360).

15. A conveyor as claimed in claim 14, in which the interposed plate comprises one or more contact pins (53) for contacting the capsule chamber (22).

16. A conveyor as claimed in claim 14, in which the or each cantilever beam has an extension.

17. A conveyor as claimed in claim 14, in which the or each cantilever beam is corrugated.

* * * * *